United States Patent [19]
Kuras et al.

[11] Patent Number: 6,162,252
[45] Date of Patent: *Dec. 19, 2000

[54] ARTIFICIAL SPINAL DISC

[75] Inventors: James M. Kuras, Macedonia, Ohio; Alexandre M. DiNello, Franklin, Mass.; Carl R. McMillin, Brecksville, Ohio

[73] Assignee: Depuy Acromed, Inc., Raynham, Mass.

[*] Notice: This patent is subject to a terminal disclaimer.

[21] Appl. No.: 08/991,224

[22] Filed: Dec. 12, 1997

[51] Int. Cl.$^7$ ........................................ A61F 2/44
[52] U.S. Cl. ...................... 623/17.16; 623/17.15
[58] Field of Search .................. 623/17, 17.11, 623/17.12, 17.13, 17.14, 17.15, 17.16, 16.11; 606/61

[56] References Cited

U.S. PATENT DOCUMENTS

| | | | |
|---|---|---|---|
| 5,071,437 | 12/1991 | Steffee | 623/17 |
| 5,534,030 | 7/1996 | Navarro et al. | 623/17 |
| 5,545,229 | 8/1996 | Parsons et al. | |
| 5,824,094 | 10/1998 | Serhan et al. | 623/17 |

Primary Examiner—V. Millin
Assistant Examiner—Hieu Phan
Attorney, Agent, or Firm—Barnes & Thornburg

[57] ABSTRACT

A spinal disc prosthesis to replace a damaged spinal disc in a spinal column of a human includes an upper rigid plate having an outer perimeter and a lower rigid plate having an outer perimeter. A body of elastomeric material located between and bonded to the upper and lower rigid plates includes a main portion and a peripheral portion extending around the main portion. The upper and lower plates each have a curved convex plate surface extending around the respective outer perimeters and facing the peripheral portion of the body of elastomeric material. The peripheral portion of the body of elastomeric material has a first part which is bonded to the curved convex plate surfaces of the upper and lower plates and extends toward the main portion. The first part of the peripheral portion increases in thickness as the first part extends from the curved convex plate surfaces toward the main portion. The first part of the peripheral portion of the body of elastomeric material has a convexly curved outer surface which forms a part of the outer surface of the body of elastomeric material.

30 Claims, 5 Drawing Sheets

ARTIFICIAL SPINAL DISC

BACKGROUND AND SUMMARY OF THE INVENTION

The present invention relates to a spinal disc prosthesis to replace a damaged or degenerated spinal disc in a spinal column of a human.

U.S. Pat. Nos. 5,017,437 and 5,534,030 disclose typical spinal disc prostheses to replace a damaged or degenerated spinal disc in a spinal column of a human. The discs disclosed in these patents include a pair of rigid plates adhered to opposite surfaces of a body of elastomeric material.

The disc when in use is positioned between adjacent vertebrae. The disc is subject to forces which act in the spine including compression forces due to loads on the spine, tension forces due to bending of the spine, and torsional forces due to twisting of the spine. These forces can be applied simultaneously to the disc. These forces act to attempt to separate the rigid plates from the body of elastomeric material.

The present invention relates to a spinal disc prosthesis to replace a damaged spinal disc in a spinal column of a human. The spinal disc prosthesis includes a body of elastomeric material located between and bonded to upper and lower rigid plates. The body of elastomeric material includes a main portion and a peripheral portion extending around the main portion.

The upper and lower plates each have a curved convex plate surface extending around the respective outer perimeters and facing the peripheral portion of the body of elastomeric material. The peripheral portion of the body of elastomeric material has a first part which is bonded to the curved convex plate surfaces of the upper and lower plates and extends toward the main portion. The first part of the peripheral portion increases in thickness as the first part extends from the curved convex plate surfaces toward the main portion. The first part of the peripheral portion of the body of elastomeric material has a convexly curved outer surface which forms a part of the outer surface of the body of elastomeric material.

BRIEF DESCRIPTION OF THE DRAWINGS

The foregoing and other features of the present invention will become more apparent to one skilled in the art upon reading the following description of a preferred embodiment with reference to the accompanying drawings, wherein.

Figures 1, 2:
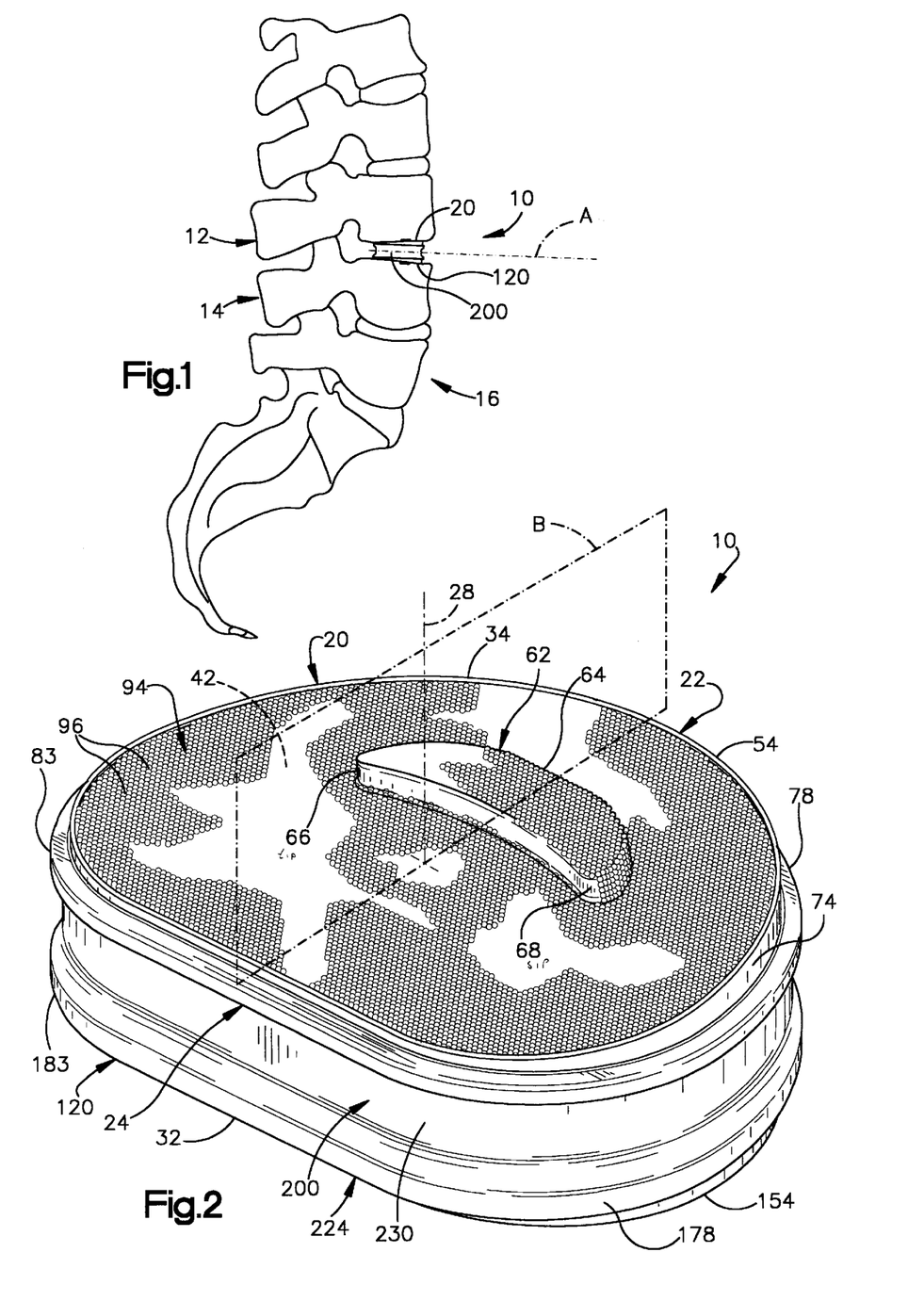
FIG. 1 is an elevational view of a human spinal column having a spinal disc in accordance with the present invention between adjacent vertebrae of the spinal column.
FIG. 2 is a top perspective view of the spinal disc of FIG. 1.

DESCRIPTION OF A PREFERRED EMBODIMENT he present invention relates to an artificial spinal disc prosthesis to replace a damaged or degenerated spinal disc in a spinal column of a human. As representative of the present invention, FIG. 1 illustrates a spinal disc prosthesis, i.e., spinal disc 10. The spinal disc 10 is illustrated in use between adjacent upper and lower vertebrae 12 and 14 of a human spinal column 16. The vertebrae 12 and 14 have portions which face anteriorly (to the right as viewed in FIG. 1) and portions which face posteriorly (to the left as viewed in FIG. 1).

Figure 3:
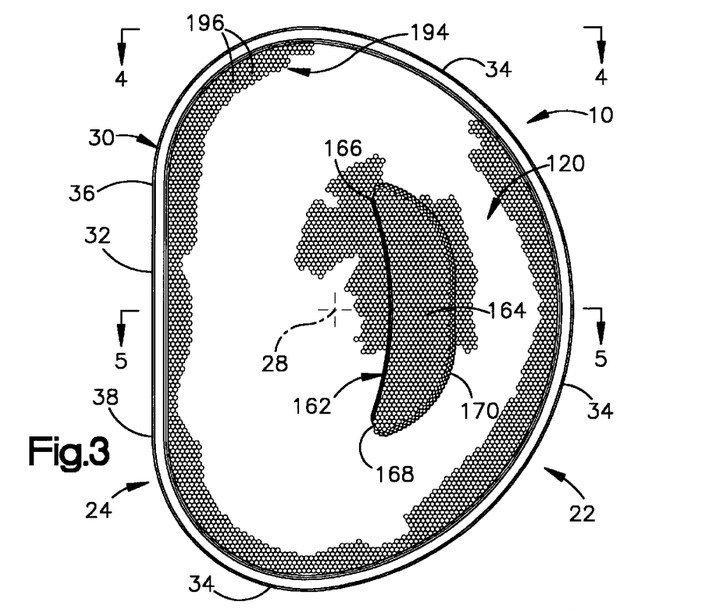
FIG. 3 is a bottom plan view of the spinal disc of FIG. 1.

The disc 10 comprises a first or upper rigid plate 20, a second or lower rigid plate 120, and an elastomeric core 200 interposed between and adhered to the two plates. The upper and lower plates 20 and 120 are identical to each other, and the disc 10 is symmetrical about an anterior-posterior, horizontally extending plane A (FIG. 4) and is also symmetrical about a sagittal plane B (FIG. 3). The terms "upper" and "lower" are used herein with reference to the orientation of the disc 10 when it is implanted in the human body as illustrated in FIG. 1, to distinguish the two identical plates for reference purposes.

The upper plate 20 (FIG. 5) is rigid and is preferably made of a biocompatible metal such as a titanium-vanadium-aluminum alloy having about 90% by weight titanium, about 6% by weight aluminum and about 4% by weight vanadium. Alternatively, the upper plate 20 can be made of any suitable biocompatible material, including but not limited to a composite plastic material. The upper plate 20 is preferably milled out of a single block of metal. The upper plate 20 could, however, be made in a different manner, for example, by casting.

The upper plate 20 has an anterior portion 22 and a posterior portion 24. The anterior portion 22 of the upper plate 20 is that portion of the upper plate which is disposed anteriorly in the spine 16 when the disc 10 is implanted in the spine. The posterior portion 24 of the upper plate 20 is that portion of the upper plate which is disposed posteriorly in the spine 16 when the disc 10 is implanted in the spine. The anterior portion of the upper plate can be said to be located generally on one side (to the right as viewed in FIG. 5) of an axis 28 of the disc 10; the posterior portion of the upper plate can be said to be located generally on the other side (to the left as viewed in FIG. 6) of the axis 28. The axis 28 extends through the disc between the upper and lower plates 20 and 120. The axis 28 extends generally along the length of the spinal column 16 when the disc 10 is implanted in the spinal column.

The configuration of the disc 10 (as viewed in plan) is designed to conform generally to the shape of a natural human spinal disc. The outer perimeter 30 (FIG. 3) of the disc 10 has a flat posterior portion 32. The outer perimeter 30 of the disc 10 has a curved convex portion 34 which extends between opposite ends 36 and 38 of the flat portion 32 of the outer perimeter. The outer perimeter 30 of the disc 10, including the outer perimeter of the core 200 and the outer perimeters 83 and 183 of the plates 20 and 120, does not have any outwardly projecting lobes. The outer perimeter of the core 200 has the same configuration (as viewed in plan) as the outer perimeter of the upper and lower plates 20 and 120.

Figure 5:
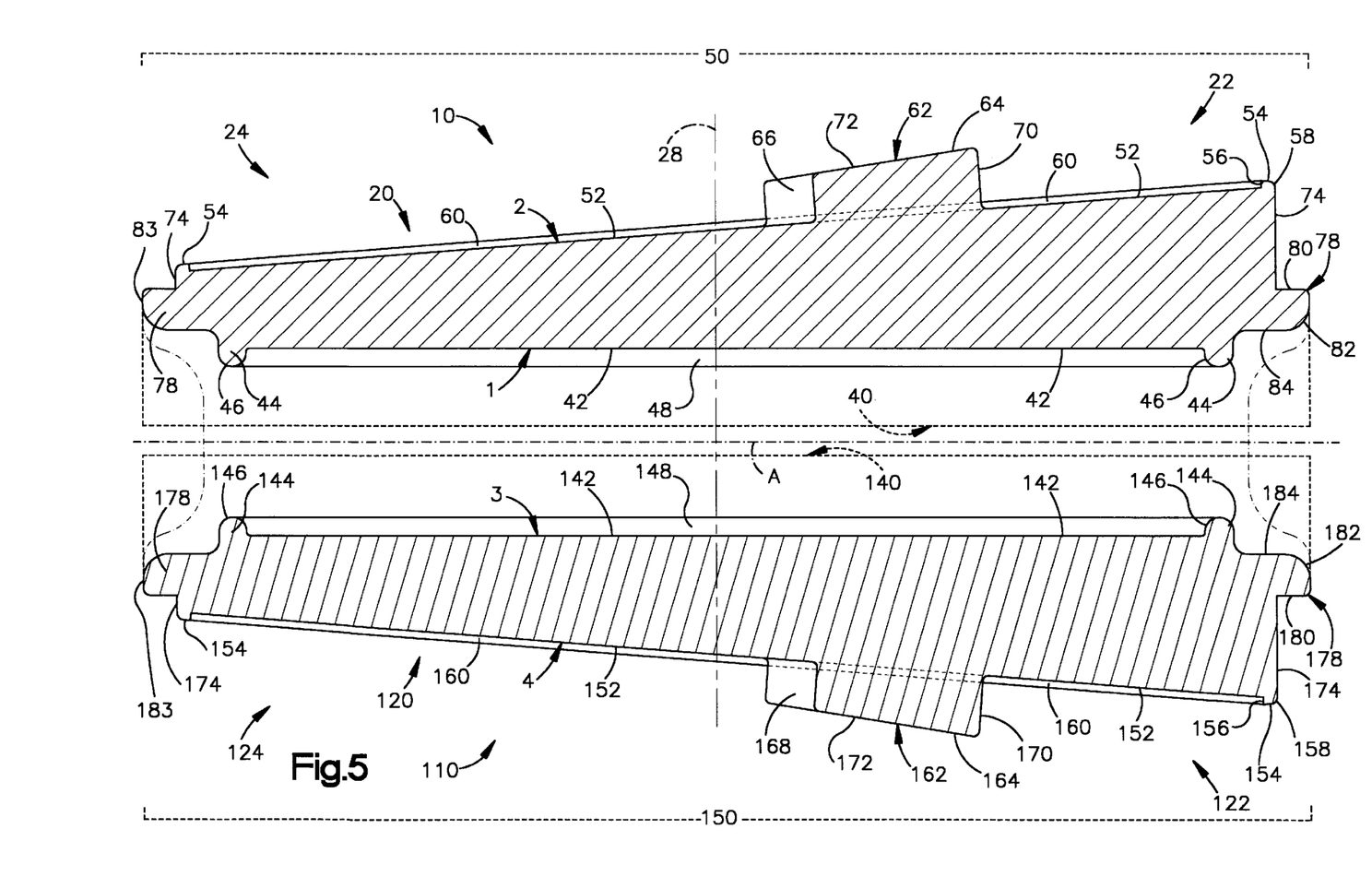
FIG. 5 is a sectional view of the spinal disc of FIG. 1, taken generally along line 5—5 of FIG. 3 and with parts removed.
Figure 6:
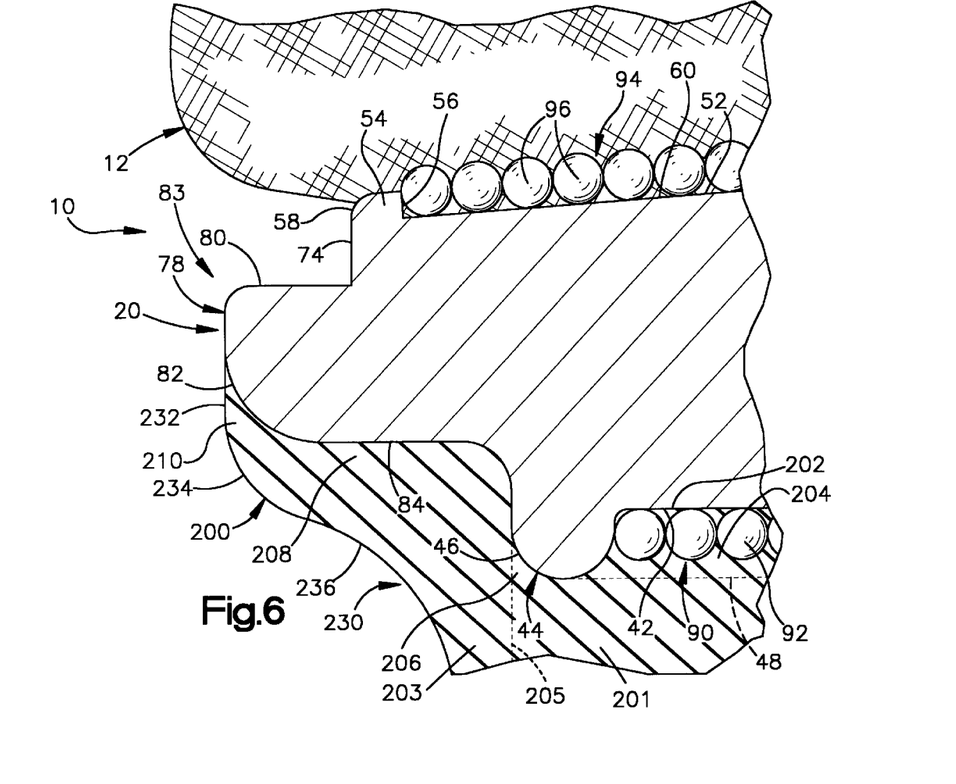
FIG. 6 is an enlarged view of a portion of FIG. 4.
Figure 7:
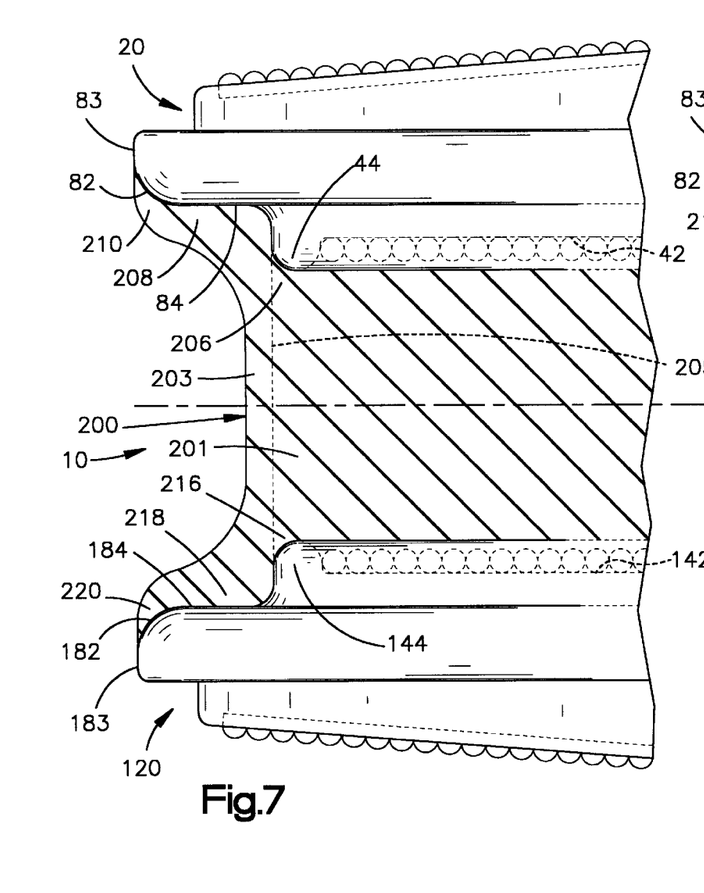
FIG. 7 is an enlarged sectional view of a portion of the spinal disc of FIG. 1, shown in a first condition.

The upper plate 20 has an inner major side surface 40 which is presented downward as viewed in FIG. 5. The inner major side surface 40 includes all of the surface area of the upper plate 20 which is visible from below (in plan) as viewed in FIG. 5. The inner major side surface 40 of the upper plate 20 includes a planar first surface 42 of the upper plate which extends perpendicular to the axis 28. The area of the first surface 42 is at least 65% of the area of the inner major side surface 40 as viewed in plan, that is, with all points on the inner major side surface 40 viewed in a direction parallel to the axis 28. Preferably, the area of the first surface 42 is 75% of the area of the inner major side surface 40.

The first surface 42 is circumscribed by a first rim 44 of the upper plate 20. The first rim 44 has a generally semi-cylindrical cross-sectional configuration as shown in FIG. 5 including an arcuate outer surface 46. The outer surface 46 on the first rim 44, and the first surface 42, together define a shallow cavity or recess 48 in the inner major side surface 40 of the upper plate 20. The first surface 42 forms the bottom of the recess 48. The outer surface 46 on the first rim 44 forms a part of the inner major side surface 40 of the upper plate 20.

The upper plate 20 has an outer major side surface 50 which is presented upward as viewed in FIG. 5. The outer major side surface 50 includes all of the surface area of the upper plate 20 which is visible from above (in plan) as viewed in FIG. 5.

The outer major side surface 50 includes a planar second surface 52 of the upper plate 20. The second surface 52 is circumscribed by a second rim 54 of the upper plate 20. The area of the second surface 52 is greater than the area of the first surface 42. The area of the second surface 52 is 85% or more, and preferably 92%, of the area of the inner major side surface 40.

The second rim 54 is located outward of (as viewed in plan) the first rim 44. The second rim 54 has an inner surface 56, which extends perpendicular to the second surface 52 and extends entirely around the upper plate 20, and a curved outer surface 58. The inner surface 56 of the second rim 54, and the second surface 52, together define a shallow cavity or recess 60 in the outer major side surface 50 of the upper plate 20. The second surface 52 forms the bottom of the recess 60.

The distance by which the second rim 54 projects from the second surface 52 is less than the distance by which the first rim 44 projects from the first surface 42. Thus, the recess 60 in the outer major side surface 50 of the upper plate 20 is shallower than the recess 48 in the inner major side surface 40 of the upper plate.

The second surface 52 of the upper plate 20 is inclined relative to the first surface 42 of the upper plate. The second surface 52 is inclined at an angle in the range of from about 1.5° to about 7.5° relative to the first surface 42. In the illustrated preferred embodiment, the second surface 52 is inclined at an angle of 5° relative to the first surface 42. In another preferred embodiment, not illustrated, the second surface 52 is inclined at an angle of 2.5° relative to the first surface 42.

Figure 4:
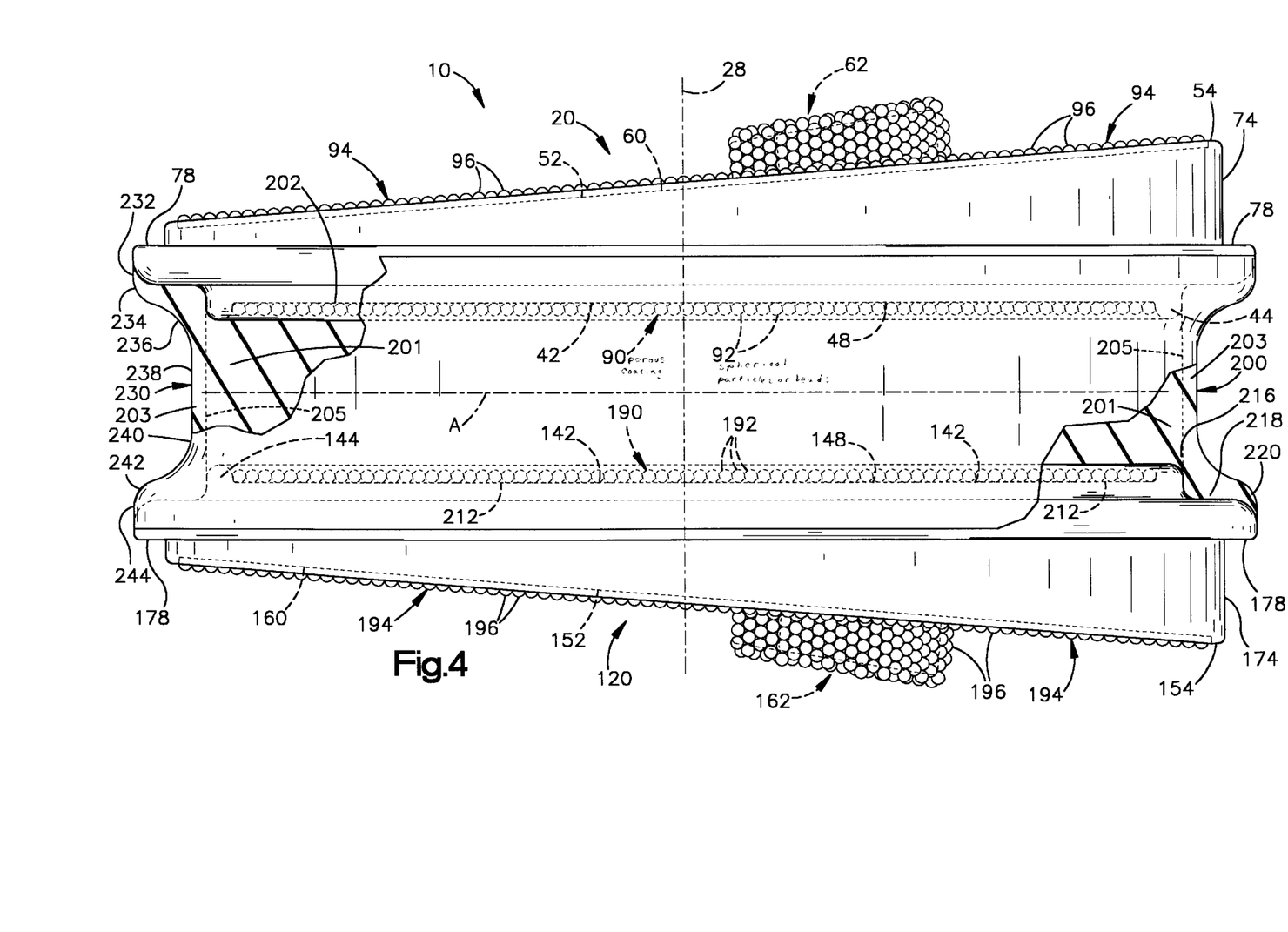
FIG. 4 is an elevational view, partly in section, of the spinal disc of FIG. 1, taken generally along line 4—4 of FIG. 3.

The first and second surfaces 42 and 52 are oriented relative to each other so that they are closest together at the posterior portion 24 of the upper plate 20, and farthest apart at the anterior portion 22 of the upper plate. The second surface 52 is inclined away from the first surface 42 as the second surface 52 extends from the posterior to the anterior of the disc 10. Thus, the first and second surfaces 42 and 52 diverge as they extend from the posterior portion 24 of the upper plate 20 to the anterior portion 22 of the upper plate. This divergence of the first and second surfaces 42 and 52 gives the upper plate 20 a wedge-shaped configuration as viewed in a lateral or medial direction (FIG. 4).

A single projection in the form of a dome 62 extends from the second surface 52 of the upper plate 20. The dome 62 has a crescent-shaped configuration including a central portion 64 and two opposite tips 66 and 68 (see FIG. 3). The dome 62 is oriented on the second surface 52 so that the tips 66 and 68 of the crescent-shaped configuration point generally posteriorly and the central portion 64 of the crescent-shaped configuration is located anteriorly of the tips. The dome 62 is also located anteriorly of the axis 28.

The outer surface 58 of the second rim 54 merges with an outer peripheral side surface 74 of the upper plate 20. The outer peripheral side surface 74 of the upper plate 20 extends perpendicular to the first surface 42 of the upper plate and also extends entirely around the upper plate. Thus, the outer peripheral side surface 74 of the upper plate 20 is not perpendicular to the plane of the second surface 52. Because of the inclination of the second surface 52 to the first surface 42, the outer peripheral side surface 74 of the upper plate 20 has a greater axial extent in the anterior portion 22 of the upper plate (to the right as viewed in FIG. 5) than in the posterior portion 24 of the upper plate (to the left as viewed in FIG. 5).

The upper plate 20 has an outer peripheral flange 78 which extends around the periphery of the upper plate. The flange 78 has a generally planar first surface 80 which extends outward from the outer peripheral side surface 74, in a direction parallel to the first surface 42. The first surface 80 of the flange 78 forms a part of the outer major side surface 50 of the upper plate 20.

The flange 78 has a curved convex second surface 82 which extends downward (as viewed in FIG. 5) and inward from the first surface 80 of the flange. The curved convex second surface 82 extends around the outer perimeter 83 of the upper plate 20. The curved convex surface 82 is disposed outward of the second surface 52 of the upper plate 20.

A planar third surface 84 of the flange 78 extends inward from the second surface 82, in a direction parallel to the first surface 80 of the flange and parallel to the first surface 42 of the upper plate 20. The third surface 84 of the flange 78 lies in a plane located between the plane of the first surface 42 of the upper plate 20 and the plane of the second surface 52 of the upper plate. The third surface 84 of the flange 78 extends from a location outward of the outer peripheral side surface 74, to a location inward of the outer peripheral side surface 74, and merges with the outer surface 46 of the first rim 44. The second and third surfaces 82 and 84 of the flange 78 form a part of the inner major side surface 40 of the upper plate 20.

A porous coating 90 (FIGS. 4 and 6) is located in the recess 48 in the inner major side surface 40 of the upper plate 20. The coating 90 is formed on the first surface 42 and is circumscribed by, or lies inward of, the first rim 44. The coating 90 covers the entire extent of the first surface 42. The coating 90 comprises a layer of small spherical particles or beads 92.

The beads 92 are preferably made of commercially pure titanium, but could be made of any suitable biocompatible material. The beads 92 are sized such that none of the beads pass through a 25 mesh U.S. Series Sieve and all the beads pass through a 40 mesh U.S. Series Sieve. The beads 92 are preferably adhered to the upper plate 20 by diffusion bonding. The beads 92 can, alternatively, be applied to the upper plate 20 by any other suitable technique.

The coating 90 of beads 92 is firmly adhered to the upper plate 20 and is incapable of removal by normal abrasions. As described below, the coating 90 in combination with a primary adhesive interlocks with the material of the elastomeric core 200 to provide a strong bond between the upper plate 20 and the elastomeric core 16. The coating 90 of beads 92 does not project past the first rim 44, that is, in a downward direction as viewed in FIG. 4 and 6.

A porous coating 94 (FIGS. 2, 4 and 6) is located in the recess 60 in the outer major side surface 50 of the upper plate 20. The coating 94 is made from beads 96 which are the same size as, and are applied in the same manner as, the beads 92 on the first surface 42. The coating 94 is formed on the second surface 52 of the upper plate 20 and is circumscribed by, or lies inward of, the second rim 54. The coating 94 covers the entire extent of the second surface 52. The coating 94 also covers the dome 62.

The coating 94 on the second surface 52, as described below, provides for ingrowth of bony tissue when the disc 10 is implanted in the spine 16. The coating 94 of beads 96 is thicker than the depth of the recess 60. Thus, the beads 96 of the coating 94 project axially outward past the second rim 54. This is in contrast to the coating 90, which does not project axially outward past the first rim 44.

The lower plate 120 is identical in configuration to the upper plate. The lower plate 120 is rigid and is made from the same material as the upper plate. The lower plate 120 (FIG. 5) has an anterior portion 122 which is disposed anteriorly in the spine 16 when the disc 10 is implanted in the spine. A posterior portion 124 of the lower plate 120 is disposed posteriorly in the spine 16 when the disc 10 is implanted in the spine.

The configuration of the lower plate 120 as viewed in plan (FIG. 3) is the same as the configuration of the upper plate 20. The outer perimeter 183 of the lower plate 120 has a flat posterior portion and a curved convex portion which extends between opposite ends and of the flat portion of the outer perimeter. The lower plate 120, like the upper plate 20, does not have any outwardly projecting lobes.

The lower plate 120 has an inner major side surface 140 (FIG. 5) which is presented upward as viewed in FIG. 5. The inner major side surface 140 includes all of the surface area of the lower plate 120 which is visible from above (in plan) as viewed in FIG. 5. The inner major side surface 140 of the lower plate 120 includes a planar third surface 142 of the lower plate 120 which extends perpendicular to the axis 28. The area of the first surface 142 is at least 65% or more of the area of the inner major side surface 140 as viewed in plan, that is, with all points on the inner major side surface 140 viewed in a direction parallel to the axis 28. Preferably, the area of the third surface 142 is 75% of the area of the inner major side surface 140.

The third surface 142 is circumscribed by a first rim 144 of the lower plate 20. The first rim 144 has a generally semi-cylindrical cross-sectional configuration as shown in FIG. 5 including an arcuate outer surface 146. The outer surface 146 on the first rim 144, and the third surface 142, together define a shallow cavity or recess 148 in the inner major side surface 140 of the lower plate 120. The third surface 142 forms the bottom of the recess 148. The outer surface 146 on the first rim 144 forms a part of the inner major side surface 140 of the lower plate 120.

The lower plate 120 has an outer major side surface 150 which is presented downward as viewed in FIG. 5. The outer major side surface 150 includes all of the surface area of the lower plate 120 which is visible from below (in plan) as viewed in FIG. 5.

The outer major side surface 150 of the lower plate 120 includes a planar fourth surface 152 of the lower plate. The fourth surface 152 is circumscribed by a second rim 154 of the lower plate 120. The area of the fourth surface 152 is greater than the area of the third surface 142. The area of the fourth surface 152 is 85% or more, and preferably 92%, of the area of the inner major side surface 140.

The second rim 154 is located outward of (as viewed in plan) the first rim 144. The second rim 154 has an inner surface 156, which extends perpendicular to the second surface 152 and extends entirely around the lower plate 120, and a curved outer surface 158. The inner surface 156 of the second rim 154, and the fourth surface 152, together define a shallow cavity or recess 160 in the outer major side surface 150 of the lower plate 120. The fourth surface 152 forms the bottom of the recess 160.

The distance by which the second rim 154 projects from the fourth surface 152 is less than the distance by which the first rim 144 projects from the third surface 142. Thus, the recess 160 in the outer major side surface 150 of the lower plate 120 is shallower than the recess 148 in the inner major side surface 140 of the lower plate.

The fourth surface 152 of the lower plate 120 is inclined relative to the third surface 142 of the lower plate. The fourth surface 152 is inclined at an angle in the range of from about 1.5° to about 7.5° relative to the third surface 142. In the illustrated preferred embodiment, the fourth surface 152 is inclined at an angle of 5° relative to the third surface 142. In another preferred embodiment, not illustrated, the fourth surface 152 is inclined at an angle of 2.5° relative to the third surface 142.

The third and fourth surfaces 142 and 152 are oriented relative to each other so that they are closest together at the posterior portion 124 of the lower plate 120, and farthest apart at the anterior portion 122 of the lower plate. The fourth surface 152 is inclined away from the third surface 142 as the fourth surface 152 extends from the posterior to the anterior of the disc 10. Thus, the third and fourth surfaces 142 and 152 diverge as they extend from the posterior portion 124 of the lower plate 120 to the anterior portion 122 of the lower plate. This divergence of the third and fourth surfaces 142 and 152 gives the lower plate 120 the same wedge-shaped configuration as the upper plate 20.

A single projection in the form of a dome 162 extends from the fourth surface 152 of the lower plate 120. The dome 162 has a crescent-shaped configuration including a central portion 164 and two opposite tips 166 and 168 (see FIG. 3). The dome 162 is oriented on the fourth surface 152 so that the tips 166 and 168 of the crescent-shaped configuration point generally posteriorly and the central portion 164 of the crescent-shaped configuration is located anteriorly of the tips. The dome 162 is also located anteriorly of the axis 28.

The outer surface 158 of the second rim 154 merges with an outer peripheral side surface 174 of the lower plate 120. The outer peripheral side surface 174 extends perpendicular to the third surface 142 of the lower plate 120 and also extends entirely around the lower plate. Thus, the outer peripheral side surface 174 of the lower plate 120 is not perpendicular to the plane of the fourth surface 152. Because of the inclination of the fourth surface 152 to the third surface 142, the outer peripheral side surface 174 of the lower plate 120 has a greater axial extent in the anterior portion 122 of the lower plate (to the right as viewed in FIG. 5) than in the posterior portion 124 of the lower plate (to the left as viewed in FIG. 5).

The lower plate 120 has an outer peripheral flange 178 which extends around the periphery of the lower plate. The flange 178 has a generally planar first surface 180 which extends outward from the outer peripheral side surface 174, in a direction parallel to the third surface 142. The first surface 180 on the flange 178 forms a part of the outer major side surface 150 of the lower plate 120.

The flange 178 has a curved second surface 182 which extends upward (as viewed in FIG. 5) and inward from the first surface 180 of the flange. The curved convex second surface 182 extends around the outer perimeter 183 of the lower plate 120. The curved convex second surface 182 is disposed outward of the second surface 152 of the lower plate 120.

A planar third surface 184 of the flange 178 extends inward from the second surface 182, in a direction parallel to the first surface 180 of the flange and parallel to the third surface 142 of the lower plate 120. The third surface 184 of the flange 178 lies in a plane located between the plane of the third surface 142 of the lower plate 120 and the plane of the fourth surface 152 of the lower plate. The third surface 184 of the flange 178 extends from a location outward of the outer peripheral side surface 174, to a location inward of the outer peripheral side surface 174, and merges with the outer surface 146 of the first rim 144. The second and third surfaces 182 and 84 of the flange 178 form a part of the inner major side surface 140 of the lower plate 120.

A porous coating 190 (FIG. 4) is located in the recess 148 in the inner major side surface 140 of the lower plate 120. The coating 190 is formed on the third surface 142 and is circumscribed by, or lies inward of, the first rim 144. The coating 190 covers the entire extent of the third surface 142. The coating 190 comprises a layer of small spherical particles or beads 192.

The beads 192 are made from the same material as the beads 92 of the coating 90. The beads 192 are preferably adhered to the lower plate 120 by diffusion bonding. The beads 192 can, alternatively, be applied to the lower plate 120 by any other suitable technique.

The coating 190 of beads 192 is firmly adhered to the lower plate 120 and is incapable of removal by normal abrasions. As described below, the coating 190 in combination with a primary adhesive interlocks with the material of the elastomeric core 200 to provide a strong bond between the lower plate 120 and the elastomeric core 16. The coating 190 of beads 192 does not project axially outward of the first rim 144.

A similar porous coating 194 (FIGS. 3 and 4) is located in the recess 60 in the outer major side surface 150 of the lower plate 120. The coating 194 is formed on the fourth surface 152 and is circumscribed by, or lies inward of, the second rim 154. The coating 194 covers the entire extent of the fourth surface 152. The coating 194 also covers the dome 162. The coating 194 is made from a plurality of beads 196 which are the same as, and are applied in the same manner as, the beads 192 on the third surface 142.

The coating 194 on the fourth surface 152, as described below, provides for ingrowth of bony tissue when the disc 10 is implanted in the spine 16. The layer 190 of beads 196 is thicker than the depth of the recess 160. Thus, the beads 196 of the coating 194 project axially outward past the second rim 154. This is in contrast to the coating 190, which does not project axially outward past the first rim 144.

The elastomeric core 200 is preferably made of a polyolefin rubber or carbon black reinforced polyolefin rubber. The hardness of the elastomeric core is 56–72 shore A durometer. The ultimate tensile strength of the core is greater than 1600 psi. The core has an ultimate elongation greater than 300% using the ASTM D412-87 testing method, and a tear resistance greater than 100 ppi using the ASTM D624-86 testing method. Although the elastomeric core 200 is disclosed as being made of a polyolefin rubber, it can be made of any elastomeric material that simulates the characteristics of a natural disc.

To construct the spinal disc 10, the plates 20 and 120, with the coatings 90, 94, 190 and 194 in place, are cleaned in a methyl ethyl ketone or similar reagent bath for approximately 25 minutes. The plates 20 and 120 are etched, for example with a nitric hydrofluoric acid solution, to remove any oxide coating from the plates. Thereafter, the plates 20 and 120 are rinsed in distilled water, and a primer is applied to the plates that will be bonded to the core 200. The primer is applied within about 2 hours of the etch, and at a nominal thickness of 0.35 mils. After the primer has dried for not less than 60 minutes, an adhesive is applied at a nominal thickness of 0.65 mils. The plates 20 and 120 are then placed in a mold and the elastomeric material of the core 200 is flowed into the mold and adhered to the plates. The elastomeric material of the core 200 is then cured to form the completed disc 10.

The elastomeric core 200 includes a main portion 201 and a peripheral portion 203, separated by an imaginary line 205 (FIGS. 4, 6, 7 and 8). The first rims 44 and 144 of the upper and lower plates 20 and 120, respectively, define the outer perimeter of the main portion 201 of the core 200. The peripheral portion 203 of the core 200 is located outward of the first rims 44 and 144 and the imaginary line 205 in FIGS. 7 and 8. The main portion 201 of the core 200 is located inward of the peripheral portion 203 of the core; the peripheral portion of the core extends around the main portion of the core.

The core 200 has a planar upper surface 202 (FIGS. 2, 4 and 6) which is affixed to and overlies the first surface 42 of the upper plate 20. A portion 204 (FIG. 6) of the material of the core 200 extends into and interlocks with the first surface 42 of the upper plate 20, as well as with the porous coating 90 on the first surface. The first surface 42 of the upper plate 20 is bonded to the upper surface 202 of the elastomeric core 200 and to the beads throughout the entire extent of the first surface.

The main portion 201 of the core 200 includes a portion 206 (FIG. 6) which extends over and is adhered to the curved outer surface 46 of the first rim 44 on the upper plate 20. As a result, the first rim 44 is bonded to the main portion 201 of the core 200.

A portion 208 of the peripheral portion 203 of the core 200 overlies the outside of the rim 44. The core portion 208 extends over and is adhered to the planar third surface 84 of the flange 78 of the upper plate 20. The core portion 208 increases in thickness as it extends from the convex second surface 82 toward the main portion 201 and the rim 44.

The peripheral portion 203 of the core includes yet another portion 210. The material portion 210 of the core 200 extends over and is adhered or bonded to the curved convex second surface 82 of the upper plate 20. The curved convex second surface 82 of the flange 78 of the upper plate 20 faces the portion 210 of the peripheral portion 203 of the core 200.

The peripheral portion 203 of the core 200 decreases in thickness as it extends from the planar third surface 84 toward the curved second surface 82 of the upper plate 20. The material portion 210 which overlies the second surface 82 of the flange 78 tapers to a zero thickness, as it approaches the first surface 80 of the flange. Conversely, the material portion 210 increases in thickness as it extends from the curved convex plate surface 82 toward the main portion 201 of the core 200, that is, in a direction to the right as viewed in FIG. 6.

The material of the core 200, as thus formed, is also affixed to the inner side surface 140 of the lower plate 120. The main portion 201 of the core 200 extends into and interlocks with the third surface 142 of the lower plate 120, as well as with the porous coating 190 on the third surface. The core 200 has a planar lower surface 212 (FIG. 4) which is affixed to the third surface 142 of the lower plate 120. The lower surface 212 of the core 200 is parallel to the upper surface 202 of the core. The third surface 142 of the lower plate 120 is bonded to the lower surface 212 of the elastomeric core 200 throughout the entire extent of the third surface.

The main portion 201 of the core 200 includes a portion 216 (FIG. 6) which extends over and is adhered to the curved outer surface 146 of the first rim 144 on the lower plate 120. As a result, the first rim 144 is bonded to the main portion 201 of the core 200.

A portion 218 of the peripheral portion 203 of the core 200 extends over and is adhered to the planar third surface 184 of the flange 178 of the lower plate 20. The core portion 218 also overlies the outer side of the first rim 144. The core portion 218 increases in thickness as it extends from the convex second surface 182 toward the rim 144 and the main portion 201. The peripheral portion 203 of the core 200 decreases in thickness as it extends from the planar third surface 184 toward the curved second surface 182 of the lower plate 120.

The peripheral portion of the core includes yet another portion 220. The material portion 220 of the core 200 extends over and is adhered or bonded to the curved convex second surface 182 of the lower plate 120. The curved convex second surface 182 of the flange 178 of the lower plate 120 faces the portion 220 of the material of the core 200. The material portion 220 which overlies the second surface 182 of the flange 178 tapers to a zero thickness, as it approaches the first surface 180 of the flange. Conversely, the material portion 220 increases in thickness as it extends from the curved convex second surface 182 toward the main portion 201 of the core 200, that is, in a direction to the left as viewed in FIG. 4.

The core 200 has an exposed outer side surface 230 (FIGS. 2, 4 and 6) which extends between the upper and lower plates 20 and 120. The outer side surface 230 of the core 200 has a generally hourglass-shaped configuration (best seen in FIG. 4) which is widest at the curved convex surfaces 82 and 182 of the upper and lower plates 20 and 120, respectively.

Specifically, the outer side surface 230 of the core 200 includes a first surface portion 232 (FIGS. 4 and 6) extending substantially perpendicular to the first surface 42 of the upper plate 20. The first surface portion 232 is located outward of the flange 78 of the upper plate 20.

A convexly curved second portion 234 of the outer side surface 230 of the core 200 extends from the first surface portion 232, in a direction toward the lower plate 120. The surface portion 234 is formed on the core material portion 210 (FIG. 6) which overlies the curved convex outer surface 82 of the upper plate 20. A concave third portion 236 of the outer side surface 230 of the core 200 extends from the second surface portion 234, in a direction toward the lower plate 120.

The outer side surface 230 of the core 200 includes an innermost or narrowest fourth surface portion 238 extending from the third surface portion 236, in a direction substantially perpendicular to the first surface 42 of the upper plate 20 and parallel to the axis 28 of the disc 10. The fourth surface portion 238 is disposed axially at a location between the upper plate 20 and the lower plate 120. The fourth surface portion 238 is disposed inward of the outer periphery of the plate flanges 78 and 178, but outward of the first rims 44 and 144 of the plates.

The fourth surface portion 238 merges with a concave fifth surface portion 240 (FIG. 4) which is a mirror image of the third surface portion 236. The fifth surface portion 240 merges with a convex sixth surface portion 242 which is a mirror image of the second surface portion 234. The sixth surface portion 242 overlies the curved convex outer surface 182 of the lower plate 120.

The sixth surface portion 242 merges with a seventh surface portion 244 which is a mirror image of the first surface portion 232. The seventh surface portion 244 is located outward of the flange 178 of the lower plate 120.

The main portion 201 of the core 200 is of substantially uniform thickness. Because the main portion 201 of the core 200 is of uniform thickness and the plates 20 and 120 are wedge-shaped, the overall configuration of the disc 10 is wedge-shaped. The disc 10 is thicker in the anterior portion 22 of the disc and is thinner in the posterior portion 24 of the disc.

When the disc 10 is in use in the spinal column 16, the upper plate 20 is affixed to the upper vertebra 12. The dome 62 on the upper plate 20 is fitted into a corresponding recess or cavity 260 (not shown) formed in the upper vertebra 12. The engagement of the dome 62 of the upper plate 20 in the cavity 260 in the upper vertebra 12 resists relative movement between the upper plate and the upper vertebra.

The porous coating 94 on the second surface 52 of the upper plate 20 promotes bone ingrowth between the upper vertebra 12 and the upper plate 20. The second surface 52 (FIG. 6) of the upper plate 20 engages the bony material of the upper vertebra 12. Interlocking engagement between the upper plate 20 and the bony material of the upper vertebra 12 is enhanced by the fact that the beads 96 of the coating 94 project axially outward past the second rim 54.

The lower plate 120 is affixed to the lower vertebra 14. The dome 162 on the lower plate 120 is fitted into a corresponding recess or cavity 262 (not shown) formed in the lower vertebra 14. The engagement of the dome 162 of the lower plate 120 in the cavity 262 in the lower vertebra 14 resists relative movement between the lower plate and the lower vertebra. The configuration of the dome 162 on the lower plate 120 has the same advantages as described above with reference to the dome 62 on the upper plate 20.

The porous coating 194 on the fourth surface 152 promotes bone ingrowth between the lower vertebra 14 and the lower plate 120. The fourth surface 152 of the lower plate 120 engages the material of the lower vertebra 14. Interlocking engagement between the lower plate 120 and the bony material of the lower vertebra 14 is enhanced by the fact that the beads 196 of the coating 194 project axially outward past the second rim 154.

Figure 8:
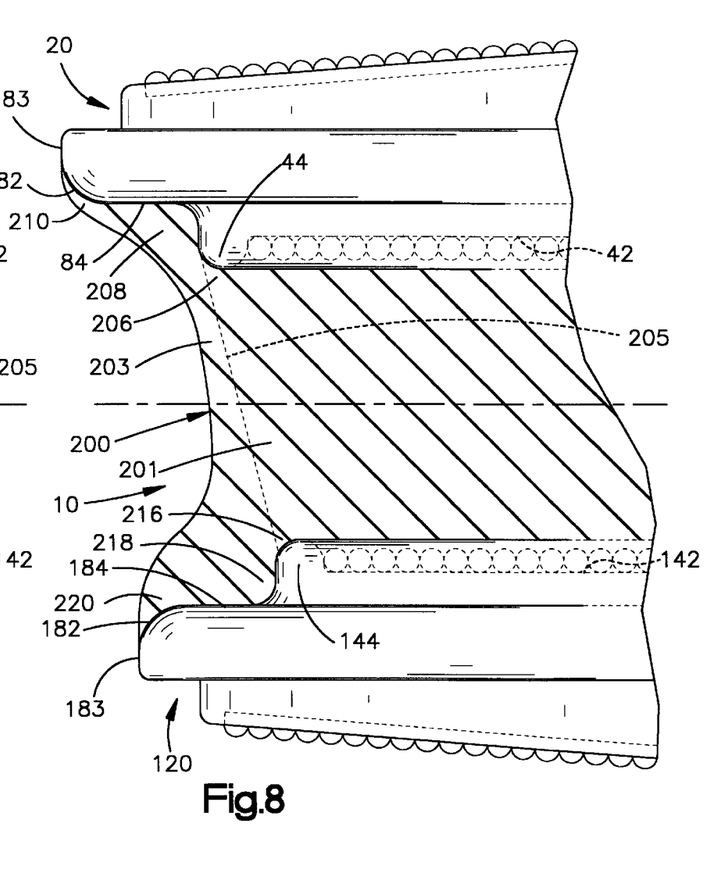
FIG. 8 is a view similar to FIG. 7 showing the spinal disc in a second condition.

The configuration of the areas of engagement between the elastomeric core 200 and the plates 20 and 120 minimizes any tendency of the plates to separate from the elastomeric core. Specifically, the molding of the perimeter of the core 200 to the curved convex outer surfaces 82 and 182 of the plates 20 and 120, respectively, helps to reduce the stress concentrations at the perimeter of the core and increases the fatigue life in cycles of the spinal disc 10 when subjected to shear deformation. Also, when the spinal disc 10 is subjected to shear stress, for example as illustrated in FIG. 8, the peripheral portion 203 of the core 200, and particularly portion 208, is a pool of elastomeric material which can stretch to absorb the stress induced on the disc 10. The stress concentrations are minimized on the main portion 201 of the core, which extends generally between the first surface 42 of the upper plate 42 and the third surface 142 of the lower plate 120.

In addition, the first rims 44 and 144 on the plates 20 and 120, respectively, with their curved outer surfaces 46 and 146, provide strain relief at the perimeter of the flat main portion 201 of the elastomeric core 200.

From the above description of the invention, those skilled in the art will perceive improvements, changes and modifications in the invention. Such improvements, changes and modifications within the skill of the art are intended to be covered by the appended claims.

Having described the invention, we claim:

1. A spinal disc prosthesis to replace a damaged spinal disc in a spinal column of a human, said spinal disc prosthesis comprising:

an upper rigid plate having an outer perimeter;

a lower rigid plate having an outer perimeter;

a body of elastomeric material located between and bonded to said upper and lower rigid plates, said body of elastomeric material including a main portion and a peripheral portion extending around said main portion;

said upper and lower plates each having a curved convex plate surface extending around said respective outer perimeters and facing said peripheral portion of said body of elastomeric material;

said peripheral portion of said body of elastomeric material having a first part which is bonded to said curved convex plate surfaces of said upper and lower plates and extends toward said main portion, said first part of said peripheral portion increasing in thickness as said first part extends from said curved convex plate surfaces toward said main portion;

said first part of said peripheral portion of said body of elastomeric material having a convexly curved outer surface which forms a part of the outer surface of said body of elastomeric material.

2. A spinal disc prosthesis as set forth in claim 1 wherein each one of said upper and lower plates has a respective rim which encircles said plate and which is bonded to said main portion of said body of elastomeric material.

3. A spinal disc prosthesis as set forth in claim 2 wherein said upper and lower plates each have a flat surface portion extending from said rim toward said curved convex plate surface, said peripheral portion of said body of elastomeric material being bonded to said flat surfaces.

4. A spinal disc prosthesis as set forth in claim 3 wherein said peripheral portion has an increasing thickness as it extends from said curved surfaces toward said flat surfaces and has a decreasing thickness as it extends from said flat surfaces toward said main portion.

5. A spinal disc prosthesis as set forth in claim 2 wherein said rims of said upper and lower plates define the outer perimeter of said main portion of said body of elastomeric material.

6. A spinal disc prosthesis as set forth in claim 5 wherein said rims of said upper and lower plates have curved outer surfaces which are bonded to said main portion of said body of elastomeric material.

7. A spinal disc prosthesis as set forth in claim 1 wherein said peripheral portion of said body of elastomeric material overlies respective flat surfaces on said upper and lower plates and overlies respective rims which encircle said plates and which are bonded to said main portion of said body of elastomeric material.

8. A spinal disc prosthesis as set forth in claim 7 wherein said peripheral portion has an increasing thickness as it extends from said curved surfaces toward said flat surfaces and has a decreasing thickness as it extends from said flat surfaces toward said main portion.

9. A spinal disc prosthesis as set forth in claim 1 wherein said main portion of said body of elastomeric material has a substantially uniform thickness across its entire extent, said peripheral portion of said body of elastomeric material having a thickness which varies as it extends outward in a direction away from said main portion of said body of elastomeric material.

10. A spinal disc prosthesis as set forth in claim 1 wherein said upper plate has an inner major side surface presented toward an inner major side surface of said lower plate, each one of said inner major side surfaces including a rim which extends around a planar first surface having an area which is at least about 90% of the area of said respective inner major side surface, said first surfaces and said rims defining the axial ends of said main portion of said body of elastomeric material.

11. A spinal disc prosthesis as set forth in claim 1 wherein each one of said upper and lower plates has a generally planar vertebral contact surface which extends outward of said main portion of said body of elastomeric material, said curved convex surfaces of said upper and lower plates being disposed outward of said vertebral contact surfaces.

12. A spinal disc prosthesis to replace a damaged spinal disc in a spinal column of a human, said spinal disc prosthesis comprising:

an upper rigid plate having an outer perimeter;

a lower rigid plate having an outer perimeter;

a body of elastomeric material located between and bonded to said upper and lower rigid plates, said body of elastomeric material including a main portion and a peripheral portion extending around said main portion;

said upper and lower plates each having a rim which encircles said plate and which is bonded to said main portion of said body of elastomeric material;

said upper and lower plates each having a curved convex plate surface extending around said outer perimeters and facing said peripheral portion of said body of elastomeric material;

said peripheral portion of said body of elastomeric material having a first part which is bonded to said curved surfaces of said upper and lower plates and extends toward said main portion, said first part of said peripheral portion increasing in thickness as said first part extends from said curved surfaces toward said main portion;

said upper and lower plates each having a flat surface extending from said curved convex plate surface toward said rim, said peripheral portion of said body of elastomeric material being bonded to said flat surfaces, said peripheral portion having an increasing thickness as it extends from said curved convex plate surfaces toward said flat surfaces and having a decreasing thickness as it extends from said flat surfaces toward said rims.

13. A spinal disc prosthesis as set forth in claim 12 wherein said body of elastomeric material has an outer surface with an hourglass-shaped configuration which is widest at said curved convex surfaces of said upper and lower plates.

14. An artificial spinal disc comprising:

upper and lower plates, each having an outer perimeter and a flange extending about the outer perimeter, and an elastomeric body located between the upper and lower plates, the body including a main portion and a peripheral portion extending about the main portion adjacent to each flange, the peripheral portion having an outer surface, a portion of which is convexly curved.

15. The disc of claim 14, wherein the peripheral portion increases in thickness as the peripheral portion extends from the flanges toward the main portion of the body.

16. The disc of claim 14, wherein each flange includes a curved convex plate surface facing the peripheral portion.

17. The disc of claim 16, wherein each plate includes a rim spaced-apart from the respective curved convex plate surface.

18. The disc of claim 17, wherein the rim is bonded to the main portion of the body.

19. The disc of claim 17, wherein each rim defines an outer perimeter of the main portion of the body.

20. The disc of claim 14, wherein the main portion of the body has a substantially uniform thickness across its entire extent.

21. The disc of claim 14, wherein each plate includes an inner major side surface that has a rim which extends around a first surface having an area which is at least about 90% of the area of the respective inner major side surface.

22. The disc of claim 21, wherein the first surfaces and the rims define the axial ends of the main portion of the body.

23. The disc of claim 14, wherein each plate has a generally planar vertebral contact surface which extends outward of the main portion of the body.

24. An artificial spinal disc comprising:

upper and lower plates, each having a rim, an outer perimeter spaced-apart from the rim, and a flange extending about the outer perimeter, and an elastomeric body located between the upper and lower plates and engaging the rims, the body including a main portion and a peripheral portion extending about the main portion adjacent to each flange, the peripheral portion varying in thickness as it extends between each flange and each rim.

25. The spinal disc of claim 24, wherein the peripheral portion includes an outer surface, a portion of which is convexly curved.

26. The spinal disc of claim 24, wherein the peripheral portion includes a first part that increases in thickness as it extends from the flange toward the main portion of the body.

27. The spinal disc of claim 24, wherein each flange includes a curved plate surface and a generally flat surface extending from the curved plate surface toward the rim.

28. The spinal disc of claim 27, wherein the peripheral portion increases in thickness as it extends from the curved plate surfaces toward the flat surfaces.

29. The spinal disc of claim 28, wherein the peripheral portion decreases in thickness as it extends from the flat surfaces toward the rims.

30. The spinal disc of claim 24, wherein the body has an hourglass-shaped outer surface.

* * * * *